United States Patent [19]

DeWoskin

[11] Patent Number: 4,734,032
[45] Date of Patent: Mar. 29, 1988

[54] ORTHODONTIC TRACTION APPLIANCE

[75] Inventor: Irvin S. DeWoskin, St. Louis County, Mo.

[73] Assignee: Orthoband Company, Inc., Barnhart, Mo.

[21] Appl. No.: 910,410

[22] Filed: Sep. 22, 1986

[51] Int. Cl.⁴ .............................................. A61C 7/00
[52] U.S. Cl. ...................................................... 433/5
[58] Field of Search ............................................ 433/5

[56] References Cited

U.S. PATENT DOCUMENTS 3,814,087 6/1974 Heikes ..................................... 433/5
4,215,983 8/1980 Frazier ..................................... 433/5

Primary Examiner—Robert Peshock
Attorney, Agent, or Firm—Senniger, Powers, Leavitt and Roedel

[57] ABSTRACT

A breakaway orthodontic traction appliance which applies traction to the teeth via tension devices comprising straps inserted in clasps having grippers for gripping the straps, the grippers opening up for pull-out of the straps from the clasps on pull on the straps exceeding a predetermined value.

10 Claims, 10 Drawing Figures

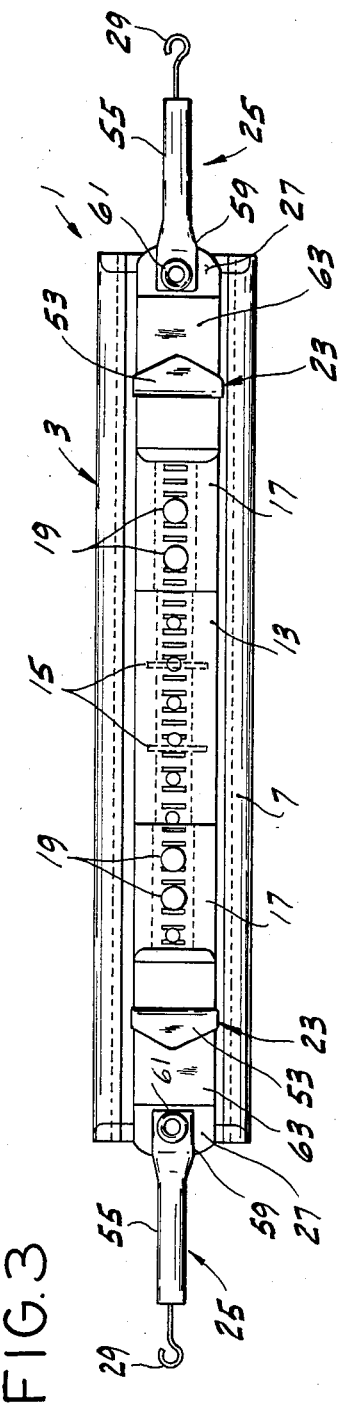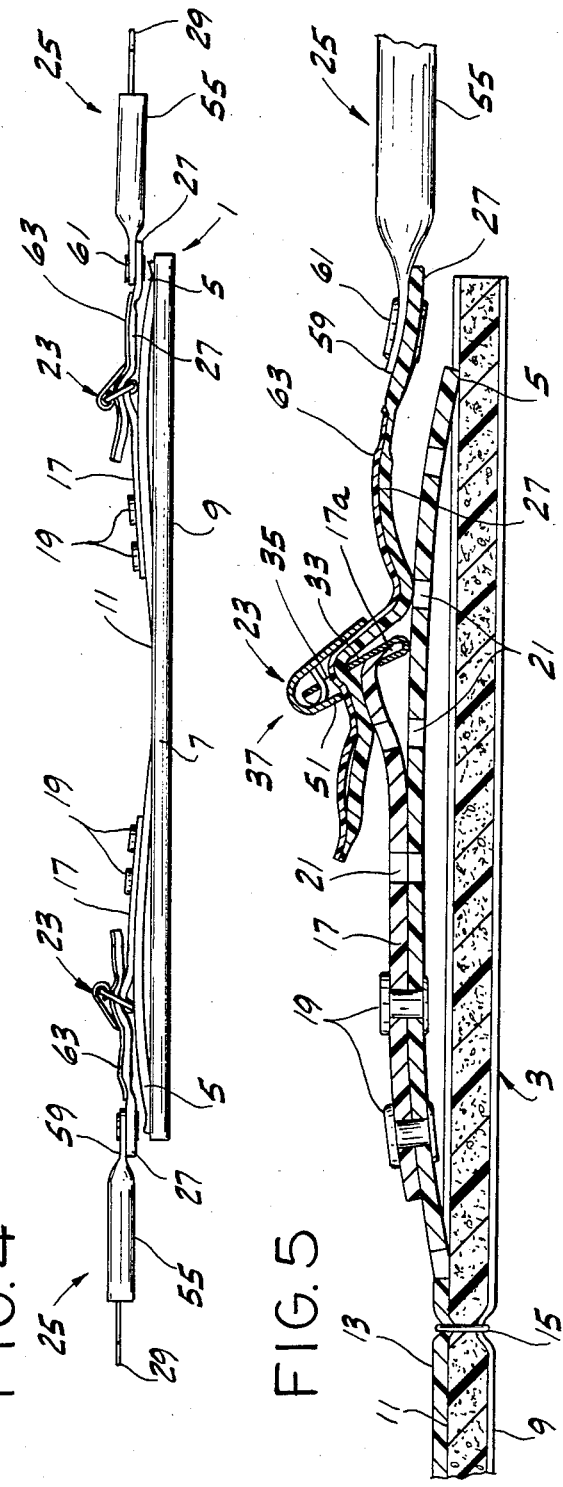

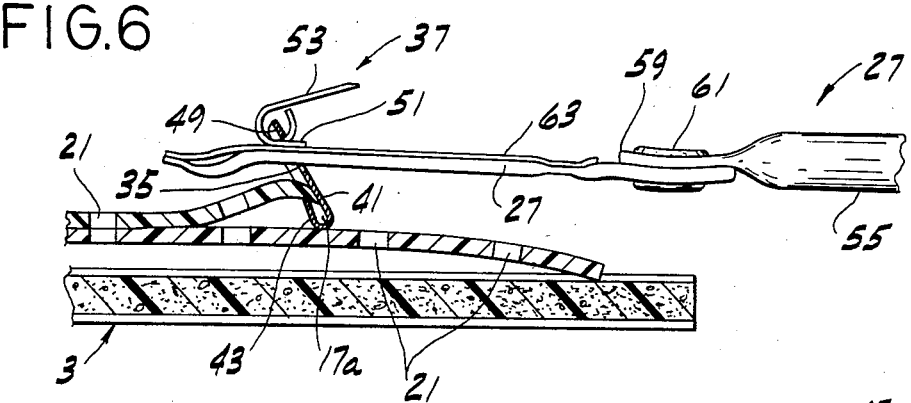
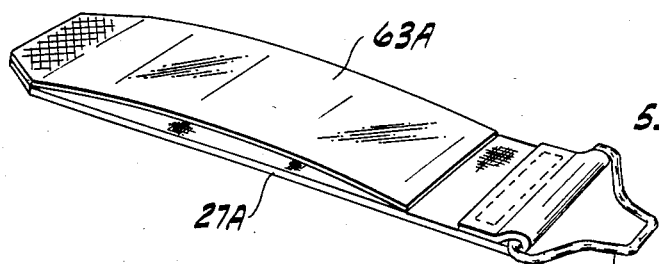
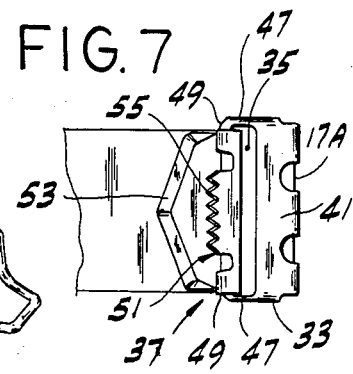
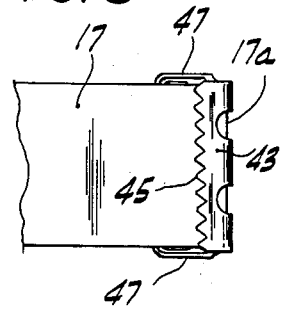
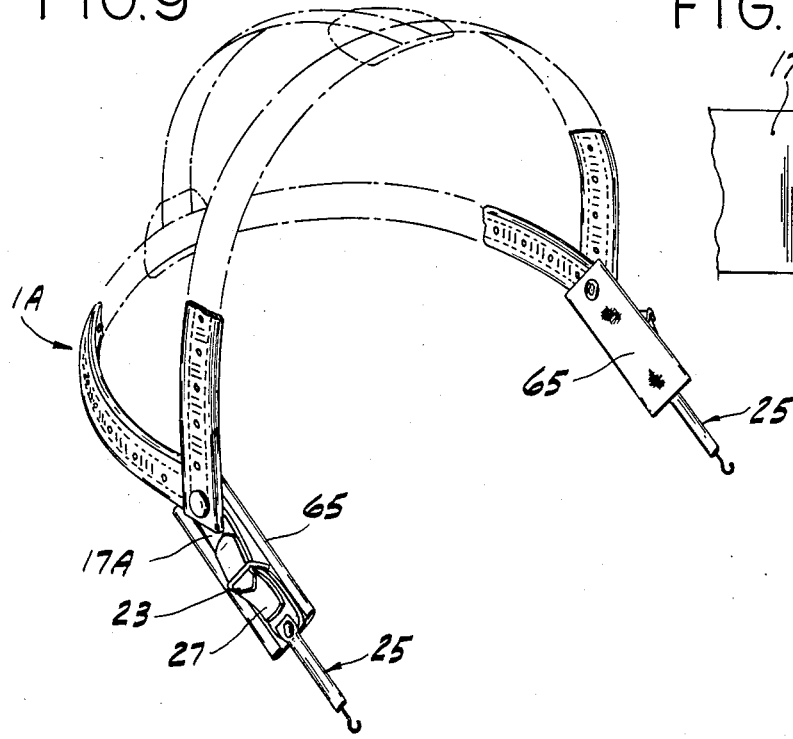

4,734,032

ORTHODONTIC TRACTION APPLIANCE

SUMMARY OF THE INVENTION

This invention relates to orthodontic traction appliances, and more particularly to such appliances with a breakaway safety feature.

The invention is especially concerned with orthodontic traction appliances of the type including headgear or a cervical strap and tension means secured to the headgear or cervical strap for exerting a pull via a face bow (an outer bow) on an arch wire (an inner bow) having free ends which are inserted in fixtures on certain of the patient's teeth to apply traction thereto. It addresses the problem discussed in U.S. Pat. Nos. 4,087,915 and 4,212,637 of avoiding injury to a patient wearing such an appliance, which may result in the event someone grasps, pulls and releases the face bow, resulting in the ends of the arch wire being pulled out of the fixtures and the arch wire springing back under the force of the tension means like a slingshot and the ends of the arch wire stabbing the patient.

Among the several objects of the invention may be noted the provision of an improved orthodontic traction appliance having a safety feature for breakaway of the face bow (and arch wire) from the tension means of the appliance in the event of excessive pull on the face bow, thereby avoiding the aforesaid slingshot effect; and the provision of an appliance such as described adapted for ready adjustment of traction and the breakaway pull; and the provision of such an appliance which is of relatively simple and economical construction, easy to use, and effective in its breakaway action.

In general, an orthodontic traction appliance of this invention comprises support means, e.g. a cervical pad or headgear to be worn by a patient, having portions which are positioned adjacent the sides of the patient's head and extensions secured to said support means extending forward adjacent opposite sides of the head as the support means is worn. Each extension has a forward end, and a clasp at said forward end. Tension means releasably secured to each extension by the respective clasp extends forward from the forward end of the respective extension as said support mean is worn. Each tension means comprises a strap, and has means at its forward end for attachment to an orthodontic face bow. Each clasp comprises a body secured to the respective extension at the forward end of the extension having an opening therein through which the respective strap is inserted from the outside with the strap extending forward from the respective extension. Each clasp further comprises gripping means carried by the clasp body for movement from an open position for insertion into and pull-out of the strap from the opening and a closed position gripping the strap inserted in the opening, the gripping means of each clasp being responsive to pull on the face bow to open and release the respective strap if the pull on the strap resulting from pull on the face bow exceeds a predetermined value.

Other objects and features will be in part apparent and in part pointed out hereinafter.

DESCRIPTION OF THE DRAWINGS

FIG. 3 is a view in elevation of the face of the device which may be referred to as its outside face;

FIG. 4 is an edge view of FIG. 3 showing clasps of the appliance closed and gripping certain straps of the appliance;

FIG. 5 is an enlarged fragment of FIG. 4 with a clasp of the appliance shown in section and shown in its closed state;

FIG. 6 is a fragment of FIG. 5 showing the clasp opened;

FIG. 7 is a view of the clasp as it appears from the outside when fully opened;

FIG. 8 is a view of the clasp as it appears from the inside;

FIG. 9 is a perspective of a second embodiment of the traction device, more particularly a high pull headgear device, as it appears when worn on the head; and FIG. 10 is a view showing a traction means for either the first or second embodiment which may be used instead of the traction mean shown in FIGS. 1-4 and 9.

Corresponding reference characters indicate corresponding parts throughout the several views of the drawings.

DETAILED DESCRIPTION

Figure 1:
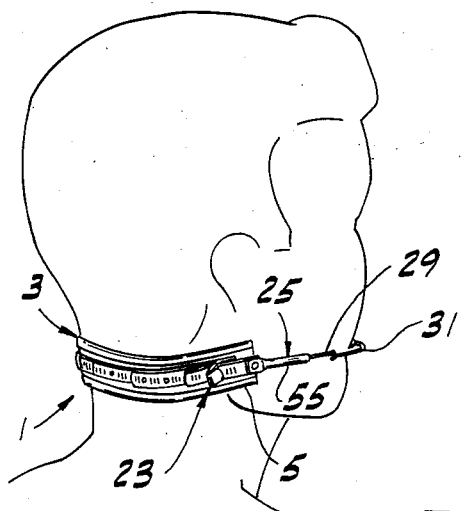
FIG. 1 is a perspective showing a first embodiment of the orthodontic traction device of this invention, more particularly an embodiment comprising a cervical pad, as worn on the patient's head.

Referring first to FIGS. 1-4 there is generally indicated at 1 an orthodontic traction appliance of this invention of the cervical type, comprising support means 3 to be worn by a patient around the back of the neck having end portions 5 which are positioned adjacent the sides of the patient's head, as said means is worn extending around the back of the neck. This cervical support means 3 comprises a pad 7 which may be of any suitable type, such as the type shown in my U.S. Pat. No. 2,874,468. The inside and outside of the strap are designated 9 and 11, respectively. Strapping 13, narrower than the cervical strap 3, is secured at the center of its length as indicated at 15 on the outside 11 of the cervical pad 7 at the center of length of the pad extending lengthwise thereof. This strapping 13 is somewhat shorter than the cervical pad. It comprises a length of inextensible strapping of any suitable type, such as the strapping shown in my U.S. Pat. No. 4,130,681, and has free ends toward the ends of the pad 7 constituting the stated end portions 5 of the said support means.

Extending from each of said end portions 5 of the strapping 13 is an extension 17, the two extensions being positioned to extend forward adjacent opposite sides of the head as the pad is worn. Each extension is constituted by an inextensible strap, which may be made from the same strapping material as the strapping 13. The extensions are secured to the said end portions 5 of the strapping 13 by means comprising fasteners 19 extending through selected holes 21 of a series of holes in the extensions and the end portions 5 of the strapping 13, enabling securing said extension straps 17 to strapping 13 in different positions of adjustment lengthwise with respect to the latter.

Figure 2:
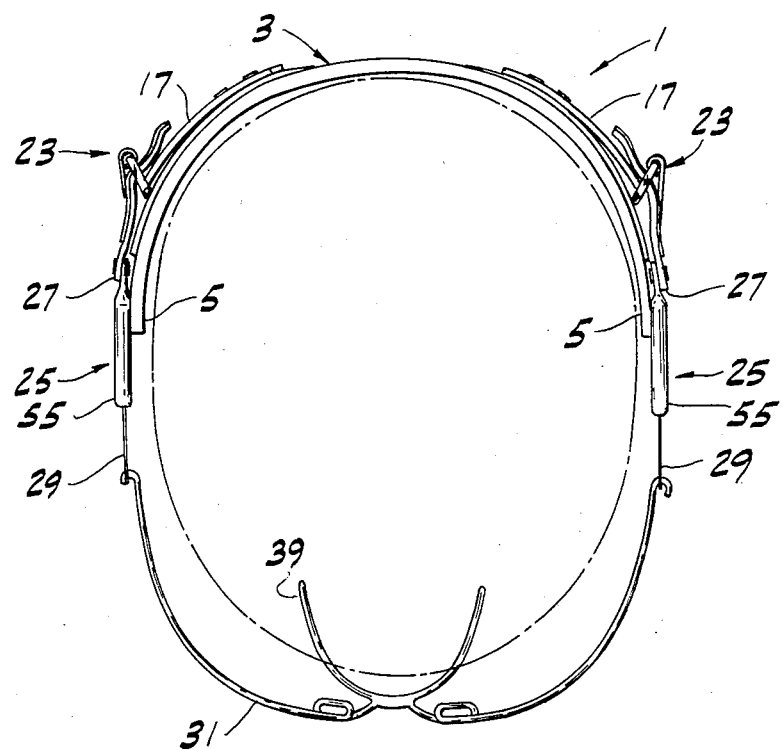
FIG. 2 is a view generally in plan showing the device as worn.

Each extension 17 has a forward end 17a (forward as the appliance is worn) and has a clasp generally designated 23 secured thereto at its forward end. Releasably secured to each of said extensions at its forward end by the respective clasp is a tension means generally designated 25, each said tension means extending forward from the forward end of the respective extension as said support means 3 is worn. Each said tension means comprises a strap 27 and has means 29 at its forward end for attachment to an orthodontic face bow 31 as shown in FIGS. 1 and 2.

Each of the clasps 23 comprises a body 33 secured to the respective adjustable extension 17 at the forward end of the extension having an opening 35 therein through which the respective strap 27 is inserted from the outside with the strap extending forward from the respective extension. The clasp further comprises gripping means 37 carried by the clasp body 33 for movement from an open position for insertion into and pullout of the strap 27 from the opening 35 and a closed position gripping the strap 27 inserted in the opening 35. The gripping means 37 of each clasp is responsive, as will appear, to pull on the face bow 31 to open and release the respective strap if the pull on the strap 27 resulting from pull on the face bow exceeds a predetermined value, that value generally being the value of the force required to pull the arch wire 39 on the face bow out of the fixtures (not shown) on the patient's teeth.

The body 33 of each clasp 23 is formed of sheet metal and comprises a generally flat crosspiece 41 which extends transversely across the respective extension 17 on the outside of the extension at its forward end, a part 43 bent to extend back under the forward end of the extension and pressed to secure the crosspiece 41 to the forward end of the extension, this part 43 having teeth as indicated at 45 which bite into the extension for firm securement of the crosspiece to the extension. The body 33 of each clasp 23 also has a pair of arms each designated 47 at the sides thereof extending back from the crosspiece. The gripping means 37 of each clasp comprises a sheet metal member pivoted as indicated at 49 at one end thereof constituting its rearward end for swinging movement on an axis extending between the rear ends of the respective arms 47, this member being formed with a part 51 constituting the gripper proper of the gripping means. The opening 35 in the clasp is defined by the crosspiece 41, the arms 47, and the gripper, the rearward edge of the crosspiece constituting the forward edge of the opening and the forward edge of the gripper constituting the rearward edge of the opening.

Each strap 27 is insertable in the opening 35 of the respective clasp body with the strap extending over the crosspiece 41 for holding of the strap by the gripper 37 against the rearward edge of the crosspiece. Each gripper 37 has a tongue 53 formed as an integral part thereof extending from the rearward end of the gripper over the gripper on the outside thereof. This tongue overlies the respective strap 27 when the strap is inserted in the opening 35 overlying the crosspiece 41 and the tongue is swung forward with the gripper. The tongue is adapted to be pressed down for causing the gripper to swing into the opening 35 and grip the strap against the rearward edge of the crosspiece, as shown in FIGS. 4 and 5, and is adapted to be swung outwardly by the strap in the direction away from the crosspiece to release the strap on excessive pull on the face bow, as shown in FIG. 6. The gripper is formed with teeth as indicated in FIG. 7 at 55 at its forward end for biting into the respective strap.

As illustrated in FIGS. 1–6, each tension means 25 includes a spring traction means 57 of the type shown in my U.S. Pat. Nos. 3,765,093, 3,772,789 and 4,121,341, each including a plastic tube which is flattened at one end as indicated at 59 and riveted as indicated at 61 at that end to the forward end of the strap 27 of said tension means on the outside of the strap extending forward from the strap. Each strap is preferably provided with a layer of flexible plastic 63 indicated on the outside where the teeth 55 bite into the strap for increased life of the strap. This layer may be constituted of a strip of 20 mil. polyurethane ether plastic suitably secured on one face of the strap (which constitutes its outside face). Means 29 comprises a rod extending from the forward end of the tube having an eye at its forward end for attachment to the face bow 31, this rod being biased rearward by a compression spring (not shown) in the tube for applying traction to the teeth via the face bow. Reference may be made to my aforesaid U.S. Pat. Nos. 3,765,093, 3,772,789 and 4,121,341 for full details re the spring traction means.

In the use of the appliance, the extensions 17 are attached to the end portions 5 of strapping 13 in a selected position of adjustment. Straps 27 of each tension means 25 are inserted in the openings 35 of the clasps 23 with these straps extending over the crosspieces 41 of the clasps on the outside of the crosspieces, and tongues 53 of the clasps are pressed in to cause the grippers 51 to grip the straps via the teeth 55 on the grippers. The pad 7 is placed on the back of the neck and the rods 29 of the tension means 25 are attached at their forward ends to the face bow as shown in FIGS. 1 and 2 for exerting traction on the teeth via the springs in the tension means, the face bow and the arch wire. In the event someone pull the face bow 31 out generally to the extent of pulling the ends of the arch wire out of the fixtures on the teeth, i.e. in the event of pull on the face bow exceeding a predetermined value, the straps 27 exert force on the tongues 53 in the direction and in the amount sufficient to swing the grippers 51 open (see FIG. 6), thereby releasing the straps for breakaway of the tension means to avoid the aforesaid sling-shot action.

FIG. 9 illustrates a second embodiment of the invention wherein the support means comprises a headgear 1A (instead of the cervical type support means 1). Extensions 17A corresponding to extensions 17 extend forward (and downward) from the headgear 1A on opposite sides of the head (on the patient's cheeks) as the headgear is worn. At the forward end of each extension 17A is a clasp 23, each clasp receiving a strap 27 carrying tension means 25 the same as in the first embodiment. The headgear is provided with cheek cushion pads each designated 65 underlying the extensions 17A and the clasps 23 at the ends of these extensions.

FIG. 10 illustrates another type of tension means that may be used instead of the tension means 25, comprising an elastic strap 27A for insertion in the clasp like strap 27, having an eye 67 at one end (its forward end) for attachment to the face bow and with plastic strip 63A (corresponding to strip 63) overlying the strap 27A attached to the other (rearward) end of the strap 27A and otherwise free of the strap 27A. With this tension means, the traction is developed by stretching the strap 27A.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An orthodonic traction appliance comprising:
   supporting means to be worn by a patient having portions which are positioned adjacent the sides of the patient's head as said support means is worn;
   extensions secured to said support means positioned to extend forward adjacent opposite sides of the head as the support means is worn, each extension having a forward end,
   a clasp at the forward end of each extension;
   tension means releasably secured to each extension by the respective clasp each extending forward from the forward end of the respective extension as said support mean is worn;
   each said tension means comprising a strap,
   each said tension means having means at its forward end for attachment to an orthodonic face bow,
   said clasp comprising a body secured to the respective extension at the forward end of the extension having an opening therein through which the respective strap is inserted from the outside with the strap extending forward from the respective extension;
   said clasp further comprising gripping means having a gripper for engagement with the strap inserted through the opening from the outside of the body to grip the strap against an edge of the clasp body at the opening,
   means mounting the gripper means on the body for movement of said gripper between an open position on the outside of said body allowing for insertion of the strap from the outside of the body into the opening and for pull-out of the strap from the opening and a closed position in engagement with the strap inserted through the opening from the outside of the body for gripping the strap against said edge of the opening,
   said gripper being so arranged as to be subject to being moved out to its open position by the strap when the strap is subjected to pull resulting from pull on the face bow exceeding a predetermined value thereby to release the strap.

2. An orthdontic traction appliance as set forth in claim 1 wherein the gripping means of each clasp is pivoted for swinging movement on an axis transverse to the respective extension and strap at the rear of said opening, the gripper being swingable on said axis to a closed position extending forward toward the front of said opening and holding the strap inserted in said opening against the clasp body at the front of the opening.

3. An orthodontic traction appliance as set forth in claim 2 wherein each said gripper is toothed at its forward end for biting into the respective strap.

4. An orthodontic traction appliance comprising:
   support means to be worn by a patient having portions which are positioned adjacent the sides of the patient's head as said support means is worn;
   extensions secured to said support means positioned to extend forward adjacent opposite sides of the head as the support means is worn, each extension having a forward end;
   a clasp at the forward end of each extension;
   tension means releasably secured to each extension by the respective clasp each extending forward from the forward end of the respective extension as said support mean is worn;
   each said tension means comprising a strap;
   each said tension means having means at its forward end for attachment to an orthodontic face bow;
   said clasp comprising a body secured to the respective extension at the forward end of the extension having an opening therein through which the respective strap is inserted from the outside with the strap extending forward from the respective extension;
   said clasp further comprising gripping means carried by the clasp body for movement from an open position for insertion into and pull-out of the strap from the opening and a closed position gripping the strap inserted in the opening;
   said gripping means of each clasp being responsive to pull on the face bow to open and release the respective strap if the pull on the strap resulting from pull on the face bow exceeds a predetermined value;
   wherein the gripping means of each clasp comprises a gripper pivoted for swinging movement on an axis transverse to the respective extension and strap at the rear of said opening, said gripper being swingable on said axis to a closed position extending forward toward the front of said opening and holding the strap inserted in said opening against the clasp body at the front of the opening; and
   wherein the body of each clasp is formed of sheet metal and comprises a generally flat crosspiece which extends transversely across the respective extension on the outside of the extension at its forward end, a part bent to extend back under the forward end of the extension and to secure the crosspiece to the forward end of the extension, and a pair of arms at the sides thereof extending back from the crosspiece, the gripper of each clasp being pivoted at one end thereof constituting its rearward end for swinging movement on an axis extending between the rear ends of the respective arms, the rearward edge of the crosspiece constituting the forward edge of the opening, each strap being insertable in the opening of the respective clasp body with the strap extending over the crosspiece on the outside of the crosspiece for holding of the strap by the respective gripper against the rearward edge of the crosspiece.

5. An orthodontic traction appliance as set forth in claim 4 wherein the gripper of each clasp has a tongue extending from the rearward end of the gripper over the gripper on the outside thereof, said tongue overlying the respective strap when the strap is inserted in the opening overlying the crosspiece and the tongue is swung forward with the gripper, said tongue being adapted to be pressed down for causing the gripper to swing into the opening and grip the strap against the rearward edge of the crosspiece, and said tongue being adapted to be swung outwardly in the direction away from the crosspiece by the strap on said excessive pull.

6. An orthodontic traction appliance as set forth in claim 5 wherein the gripper and tongue of each clasp are formed in one piece of sheet metal, each gripper being formed with teeth at its forward end for biting into the respective strap.

7. An orthdontic traction appliance as set forth in claim 1 wherein the strap of each said tension means is generally inextensible, and each said tension means includes a spring traction means extending forward from the forward end of the respective strap.

8. An orthdontic traction appliance as set forth in claim 1 wherein the strap of each said tension means is an elastic traction strap.

9. An orthdontic traction appliance as set forth in claim 1 wherein said support means comprises a cervical pad, strapping secured to the cervical pad on the outside thereof and having free ends toward the ends of the pad constituting said portions of said support means, said extensions comprising straps extending from the free ends of said strapping, and said appliance having means for securing said extension straps to said strapping in different positions of adjustment lengthwise with respect to said strapping.

10. An orthdontic traction appliance as set forth in claim 1 wherein said support means comprises a headgear, said extensions comprising straps extending forward from said headgear and said appliance having cheek cushion pads underlying said extensions and the clasps at the ends of the extensions.

* * * * *